US005843923A

United States Patent [19]

Schleck et al.

[11] Patent Number: 5,843,923

[45] Date of Patent: Dec. 1, 1998

[54] GLUCOSAMINE SULFATE POTASSIUM CHLORIDE AND PROCESS OF PREPARATION THEREOF

[75] Inventors: James R. Schleck, Somerset; Christopher M. Burger, Toms River; Vilas M. Chopdekar, Edison, all of N.J.

[73] Assignee: Jame Fine Chemicals, Inc., Bound Brook, N.J.

[21] Appl. No.: 83,173

[22] Filed: May 22, 1998

[51] Int. Cl.[6] .............................. C07H 5/06; A01N 43/04

[52] U.S. Cl. ................................................................ 514/62

[58] Field of Search ................................. 536/18.7, 55.2; 514/23, 62

[56] References Cited

U.S. PATENT DOCUMENTS

| | | |
|---|---|---|
| 3,683,076 | 8/1972 | Rovati . |
| 4,642,340 | 2/1987 | Senin et al. . |
| 5,663,415 | 9/1997 | Chopdekar et al. . |

FOREIGN PATENT DOCUMENTS

| | | |
|---|---|---|
| 0214642 | 3/1987 | European Pat. Off. . |

*Primary Examiner*—James O. Wilson
*Assistant Examiner*—Howard Owens
*Attorney, Agent, or Firm*—Jack Matalon

[57] ABSTRACT

A composition comprising the compound glucosamine sulfate potassium chloride having a purity level of at least about 97% and water present in a maximum amount of about 10 wt. %, based on the weight of the composition. The compound is prepared by contacting glucosamine hydrochloride with potassium sulfate in the presence of water to form an aqueous solution of glucosamine sulfate potassium chloride and thereafter freeze-drying the solution at a temperature and at a reduced pressure for such period of time that at least about 90 wt. % of the water is removed and decomposition of the compound glucosamine sulfate potassium chloride is limited to a maximum of about 3%.

12 Claims, No Drawings

GLUCOSAMINE SULFATE POTASSIUM CHLORIDE AND PROCESS OF PREPARATION THEREOF

FIELD OF INVENTION

The invention relates to a composition comprising glucosamine sulfate potassium chloride and a process for preparing same. The glucosamine sulfate potassium chloride is a pure compound having a purity level of at least about 97%.

BACKGROUND OF THE INVENTION

Glucosamine sulfate is a well known and widely used substance for the treatment of rheumatic fever, arthritic and arthosic complaints, in the acute as well as chronic forms, as well as in the treatment of pathological conditions originating from metabolic disorders of the osteo-articular tissue.

Mixed salts of glucosamine sulfate and alkaline or earth alkaline metal halides such as potassium chloride, and sodium chloride are well known. Such mixed salts are used rather than glucosamine sulfate alone since the latter is unstable in view of its highly hygroscopic nature and the facility with which its amino group oxidizes if not completely saltified, see e.g. U.S. Pat. No. 4,642,340. U.S. Pat. No. 3,683,076 discloses a mixture of glucosamine sulfate and glucosamine hydroiodide for the treatment of osteoarthritis and rheumatoid arthritis.

Free glucosamine base may be prepared by the method recited in *Chem. Ber.,* volume 75, page 1274. Such method involves the treatment of glucosamine hydrochloride with an ethanolic solution of a tertiary base such as triethylamine. Triethylamine hydrochloride is filtered off and the free glucosamine is then recovered from the reaction mixture. However, triethylamine is a toxic material even in small quantities and the yield of the free glucosamine base is quite low.

In EP 0 214 642, free glucosamine base is converted to a mixed salt of glucosamine sulfate and potassium chloride by dissolving the glucosamine base in water, adding a stoichiometric quantity of concentrated sulfuric acid to form a solution of glucosamine sulfate in water and dissolving a stoichiometric amount of potassium chloride in the solution. The mixed salt is precipitated from the solution by addition of a precipitant such as isopropanol, stirring the mixture for about 14 hours to complete the precipitation, cooling the reaction mass to 0° C. and recovering the precipitated salt by filtration. This process results in low yields.

SUMMARY OF THE INVENTION

It has now been found possible to prepare a composition comprising a pure compound, and not a salt mixture, of glucosamine sulfate potassium chloride. The compound will have a purity level of about 97%, preferably at least 99%. Moreover, the process of the invention avoids the use of toxic reagents such as triethylamine and also avoids the use of precipitants such as isopropanol, thereby permitting substantially quantitative yields with little or no impurities present other than very minor quantities of water.

DETAILS OF THE INVENTION

The invention pertains to a novel composition and a process for preparing same. The composition comprises:

(a) the compound glucosamine sulfate potassium chloride having a purity level of at least about 97%; and (b) water, present in a maximum amount of about 10 wt. %, based on the weight of the composition.

Preferably, the compound will have a purity level of at least 99%. Indeed, the process of the invention typically results in a compound having a purity level in excess of 99%. The principal impurity will be water which is preferably present in a maximum amount of 5 wt. %, based on the weight of the composition. Typically, the process of the invention will produce a composition with a water content of not greater than 3 wt. %.

Any water present in the composition of the invention is not to be regarded as an "impurity" in the classical sense. The composition of the invention is intended to be ingested and minor adjustments in the dosage to be ingested can be readily made to account for such water.

Commercially available compositions of glucosamine sulfate and potassium chloride will have a density in excess of 1.10 g/cc and, as discussed below, appear to be a mixture of glucosamine hydrochloride and potassium sulfate rather than the compound glucosamine sulfate potassium chloride. Glucosamine sulfate potassium chloride prepared using isopropanol or acetone as a precipitant exhibited unacceptable glucosamine hydrochloride assay values of about 93% and densities of 0.55–0.65, indicating that some potassium chloride is abstracted from the composition and remains in the aqueous precipitant layer.

The compound glucosamine sulfate potassium chloride of the invention has a density of less than about 1.10 g/cc, preferably in the range of 0.90 to 1.00 g/cc. As discussed below in respect to Table I, the glucosamine hydrochloride assay value of the compound of the invention remains about 100 wt. %, prior to and subsequent to nitrogen sparging, which indicates that a true compound, rather than a mixture of salts or a mixture of reacted components plus unreacted components has been prepared by the process of the invention.

The process for preparing the novel composition of the invention is quite simple and straightforward and typically results in quantitative yields. The process involves the following steps:

(a) contacting glucosamine hydrochloride with potassium sulfate in the presence of water to form an aqueous solution of glucosamine sulfate potassium chloride; and (b) recovering the compound by freeze-drying the solution from step (a) at a temperature and at a reduced pressure for such period of time that: (i) at least about 90 wt. % of the water is removed and (ii) decomposition of the compound glucosamine sulfate potassium chloride is limited to a maximum of about 3 wt. %.

Typically, the glucosamine hydrochloride and potassium sulfate are contacted in stoichiometric quantities in the presence of sufficient water to form a concentration of solids of about 15 to 40 wt. %, preferably 20 to 30 wt. %, and the contacting takes place for a period of about 15 minutes to 2 hours. Step (a) takes place at temperatures, e.g. 20° to 50° C.

The freeze-drying in step (b) is typically carried out at a pressure of not greater than about 800 milliTorr, preferably 300 to 500 milliTorr, and at a temperature in the range of about −60° C. to 0° C., preferably −40° to −5° C.

The process of the invention avoids the use of precipitants such as isopropanol, acetone, dioxane, etc. in order to recover the glucosamine sulfate potassium chloride from the aqueous reaction mixture.

It has also been found that if distillation instead of freeze-drying is used to recover the glucosamine sulfate potassium chloride, some decomposition of the product occurs, even if the distillation is carried out at moderate temperatures of about 65° C. and under vacuum at a pressure of about 20 mm Hg. Decomposition of the product is evidenced by a yellowing of the product and a shift in taste from sweetish and slightly salty to a bitter taste. When the water was attempted to be removed under vacuum at a pressure of about 20 mm Hg at ambient temperatures, significant foaming of the reaction mass occurred which prevented the water from being distilled off without also causing the product to flow out of the flask containing the aqueous solution.

The following non-limiting examples shall serve to illustrate the various embodiments of this invention. Unless otherwise indicated to the contrary, all parts and percentages are on a weight basis.

EXAMPLE 1

The purpose of this example was to prepare an aqueous solution of glucosamine sulfate potassium chloride and isolate the product by removing the water by vacuum distillation.

A one-liter, three-necked flask equipped with a thermometer, stirrer, heating mantle and condenser was charged with 352.7 g of purified water, 107.8 g (0.5 mole) of glucosamine hydrochloride. The glucosamine hydrochloride promptly went into solution, with stirring (the dissolution of the glucosamine hydrochloride was endothermic in nature). After stirring for a few minutes, 43.5 g (0.25 mole) of potassium sulfate was added to the solution and stirring was continued for about one hour at 35°–40° C. to complete the reaction.

The clear solution was transferred to a one-liter single-neck flask and water was stripped off at 60°–65° C. under a vacuum of approximately 20 mm Hg. It was noticed that the product turned progressively yellow in color as the water was being stripped off. The product was dried under vacuum at 70° C. for 8 hours. The product assay, by titration, was 98.5%. The yield of product was 147.5 g (97.5% of theory). However, the product had a yellow-orange color and was therefore not deemed to be acceptable, notwithstanding that the assay and yield were good.

EXAMPLE 2

The equipment described in Example 1 was employed in this example. 56 g (0.26 mole) of glucosamine hydrochloride and 200 ml of isopropanol were charged to the flask, resulting in a slurry. 25.2 g (0.25 mole) of triethylamine were added over a 1-hour period and stirring continued for 24 hours at 25° C. and thereafter filtered. Gas chromatographic analysis of the filtrate indicated the presence of free triethylamine which is a toxic material.

EXAMPLE 3

This example was carried out to demonstrate the process of the invention. Example 1 was repeated up to the point of obtaining the clear solution of glucosamine sulfate potassium chloride. The water was then stripped off from the clear solution by freeze-drying under the following conditions:

The freeze temperature was set at −40° C., the condenser set point was −45° C., the vacuum set point was 200.0 milliTorr and the vacuum safety was set at 800 milliTorr. The solution was then subjected to the following freeze-drying steps:

| Step | Temp. °C. | Time, minutes |
|---|---|---|
| 1 | −30 | 120 |
| 2 | −15 | 300 |
| 3 | −5 | 540 |
| 4 | 0 | 540 |
| 5 | 10 | 300 |
| 6 | 20 | 240 |
| Post Heat | 25 | 60 |

A white powder was obtained in a yield of 98.5% of theoretical; the assay of the product was 100.3%.

EXAMPLE 4

This example was carried out to prepare glucosamine sulfate potassium chloride by the prior art method of precipitation using isopropanol.

The same equipment as employed in Example 1 was used for this Example. 25.9 g (0.12 m) of glucosamine hydrochloride was added to 84 g of purified water in the flask and the mixture was stirred to obtain a clear solution. 10.6 g of potassium sulfate was added to the solution and stirring was continued for 1 hour at 25°–30° C. Thereafter, 336 g of isopropanol were added to precipitate the glucosamine sulfate potassium chloride. The reaction mixture was maintained at 20° C. for 4 hours and the product was recovered by filtration. The product was washed with 100 g of isopropanol and dried under vacuum. The yield was 31 g (85.4% of theory). The product was then assayed by titration and the assay result was 93%, which was not deemed to be acceptable.

The results of this example indicate that precipitation of glucosamine sulfate potassium chloride is undesirable in several respects: low yield, poor volume efficiency, high solvent disposal cost, low product assay and the possibility of contamination of the final product with residual isopropanol.

EXAMPLE 5

This example was carried out to prepare glucosamine sulfate potassium chloride by the prior art method of precipitation using acetone.

Example 4 was repeated using 336 g of acetone to precipitate the product. The product yield was 32.6 g (90% of theory). The product was assayed by titration and the assay result was 93.4% which was deemed to be unacceptable.

EXAMPLE 6

The purpose of this example was to compare glucosamine sulfate potassium chloride obtained (a) by preparing a synthetic mixture of solid glucosamine hydrochloride and potassium sulfate, (b) from various commercial sources and (c) from Examples 4 and 5 with that prepared by the freeze-dried process of the invention exemplified by Example 3.

The synthetic mixture was prepared by thoroughly mixing (but not milling) 400 g of glucosamine hydrochloride with 160 g of potassium sulfate. The particular method by which the various commercial-sourced glucosamine sulfate potassium chloride samples were prepared was not known. However, based on the results set forth in Table I below, it appears that the commercial-sourced glucosamine sulfate potassium chloride was prepared by thoroughly mixing stoichiometric amounts of glucosamine hydrochloride and potassium sulfate.

To demonstrate that the glucosamine sulfate potassium chloride of the invention differed from the synthetic salt mixture, samples of the two materials were subjected to X-Ray Diffraction Analysis using a Dexco 8532/8806 x-ray diffractometer. The samples were scanned from 5°–65° 2θ. The four most intense peaks are set forth below:

| | Intensity | |
|---|---|---|
| Peak | GSPC* Freeze-Dried | GSPC* Synthetic Mixture |
| 100% Peak | 7.396 | 5.210 |
| 2nd Peak | 2.930 | 3.335 |
| 3rd Peak | 3.919 | 7.340 |
| 4th Peak | 3.688 | 3.745 |

*GSPC = Glucosamine Sulfate Potassium Chloride

The comparison of the various materials was carried out using the following procedure: A 1-liter glass beaker was provided with a paper thimble of 12.1 cm in length and 4.4 cm in diameter. A glass tube with a fritted end having a length of 25.4 cm, an outer diameter of 7.6 mm and an inner diameter of 5.1 mm was inserted into the thimble such that the end thereof was approximately 5 mm from the bottom of the thimble. Glucosamine sulfate potassium chloride in the amount of 50 g from various sources was placed in the thimble and the open end of the glass tube was connected to a nitrogen gas cylinder. Nitrogen was sparged through the frit at the rate of 56.6 liters/minute for approximately 15 minutes and lighter material cascaded over the thimble and was collected in the beaker. The material in the thimble was measured for its density and assayed by titration for glucosamine hydrochloride prior to commencement of nitrogen sparging. The fraction sparged out was also measured for specific rotation and assayed. The fraction remaining in the thimble was also measured for specific rotation. Table I set forth below indicates the results.

TABLE I

| GSPC* | | Density | Initial | Fraction Out | | Remaining Fraction |
|---|---|---|---|---|---|---|
| Source | Appearance | g/cc | Assay | Sp. Rot. | Assay | Sp. Rot. |
| Synth. Mixture | White Crystals | 1.20 | 98.6% | 67.52 | 131.8% | 26.80 |
| Ex. 3 | White Fine Powder | 0.92 | 100.3% | 50.90 | 100.1% | 52.71 |
| Ex. 4 | White Fluffy Powder | 0.58 | 93.0% | 50.30 | 90.6% | 50.23 |
| Ex. 5 | White Fluffy Powder | 0.61 | 93.4% | 53.49 | 95.5% | 52.01 |
| Comm'l A | White Fine Powder | 1.16 | 100.2% | 62.10 | 118.0% | 42.10 |
| Comm'l B | White Fine Powder | 1.21 | 100.7% | 62.65 | 119.7% | 41.54 |
| Comm'l C | White Cryst. Powder | 1.22 | 100.4% | 62.17 | 118.6% | 42.03 |
| Comm'l D | White Crystals | 1.15 | 106.7% | 65.65 | 128.1% | 28.60 |

GSPC* = Glucosamine Sulfate Potassium Chloride

The following conclusions may be drawn from the results set forth in Table I:

1. Based on appearance and density, commercial samples A–D were identical compositions. Furthermore, based on such factors, the commercial samples appeared to be of the same composition as the synthetic mixture.
2. For the synthetic mixtures and the commercial samples, the initial assays, i.e. before nitrogen sparging, were all satisfactory. However, after sparging, the assays obtained from the material sparged out of the thimble were considerably different from the initial assays indicating that the compositions were not true compounds. This was further reinforced by the different specific rotation values obtained in respect to the material sparged out versus those of the material remaining in the thimble.
3. The compositions of Examples 4 and 5 obtained by isopropanol and acetone precipitants, respectively, had unacceptable initial assays and very low densities. Such results are indicative that some potassium chloride had been abstracted from the compositions and remained dissolved in the aqueous precipitant filtrate. Thus, although the initial assays were comparable to those of the materials sparged out tending to indicate that a compound rather than a mixture was present, such compound nevertheless had an unacceptably low purity level.
4. The Example 3 composition prepared by the process of the invention was a highly pure true compound in all respects, i.e. density, initial assay, assay of the material being sparged out and comparable specific rotation values of the material sparged out and that remaining in the thimble.

What is claimed is:

1. A composition comprising:

(a) the compound glucosamine sulfate potassium chloride, said compound having a purity level of at least about 97%; and (b) water, present in a maximum amount of about 10 wt. %, based on the weight of the composition.

2. The composition of claim 1 wherein the purity level is at least 99%.

3. The composition of claim 1 wherein water is present in a maximum amount of 5 wt. %, based on the weight of the composition.

4. The composition of claim 3 wherein the water is present in a maximum amount of 3 wt. %, based on the weight of the composition.

5. The composition of claim 1 having a density of less than about 1.10 g/cc.

6. The composition of claim 5 wherein the density is in the range of 0.90 to 1.00 g/cc.

7. A process for preparing a composition comprising the compound glucosamine sulfate potassium chloride, said compound having a purity level of at least about 97%, which comprises the steps of:

(a) contacting glucosamine hydrochloride with potassium sulfate in the presence of water to form an aqueous solution of glucosamine sulfate potassium chloride; and (b) recovering the compound by freeze-drying the solution from step (a) at a temperature and at a reduced pressure for such period of time that: (i) at least about 90 wt. % of the water is removed and (ii) decomposition of the compound glucosamine sulfate potassium chloride is limited to a maximum of about 3%.

8. The process of claim 7 wherein the glucosamine hydrochloride and potassium sulfate are contacted in stoichiometric quantities in the presence of sufficient water to form a concentration of solids of about 15 to 40 wt. %, and the contact takes place for a period of about 15 minutes to 2 hours.

9. The process of claim 8 wherein the water is present in an amount such that the concentration of solids is in the range of 20 to 30 wt. %, based on the weight of water plus solids.

10. The process of claim 7 wherein step (a) takes place at a temperature in the range of 20° to 50° C.

11. The process of claim 7 wherein the freeze-drying is carried out at a pressure of not greater than about 800 milliTorr and at a temperature in the range of about −60° C. to 0° C.

12. The process of claim 11 wherein the freeze-drying is carried out at a pressure in the range of 300 to 500 milliTorr and a temperature in the range of −40° to −5° C.

* * * * *